United States Patent [19]

Bissett

[11] Patent Number: 5,681,852

[45] Date of Patent: Oct. 28, 1997

[54] DESQUAMATION COMPOSITIONS

[75] Inventor: Donald L. Bissett, Hamilton, Ohio

[73] Assignee: The Procter & Gamble Company, Cincinnati, Ohio

[21] Appl. No.: 480,632

[22] Filed: Jun. 7, 1995

Related U.S. Application Data

[63] Continuation-in-part of Ser. No. 558,944, Nov. 13, 1995, which is a continuation of Ser. No. 209,041, Mar. 9, 1994, abandoned, which is a continuation-in-part of Ser. No. 150,942, Nov. 12, 1993, abandoned.

[51] Int. Cl.$^6$ ............... A61K 31/095; A61K 31/16; A61K 31/195; A61K 31/205
[52] U.S. Cl. ............... 514/556; 514/562; 514/625; 514/706; 514/859
[58] Field of Search ............... 514/556, 562, 514/859, 706, 625

[56] References Cited

U.S. PATENT DOCUMENTS

| 3,647,834 | 3/1972 | Martin et al. | 514/859 |
|---|---|---|---|
| 4,411,886 | 10/1983 | Hostettler | 424/70 |
| 4,847,071 | 7/1989 | Bissett et al. | 424/59 |
| 4,847,072 | 7/1989 | Bissett et al. | 424/59 |
| 5,296,500 | 3/1994 | Hillebrand | 514/562 |

FOREIGN PATENT DOCUMENTS

| 0281812 | 9/1988 | European Pat. Off. |
|---|---|---|
| 0299756A2 | 1/1989 | European Pat. Off. |
| 0633308 A1 | 1/1995 | European Pat. Off. |
| 56-147708 | 11/1981 | Japan |
| 59-5107 | 1/1984 | Japan |
| 06092833 | 4/1994 | Japan |
| 06135825 | 5/1994 | Japan |
| 6157257 | 6/1994 | Japan |
| 1518683 | 7/1978 | United Kingdom |
| 91/17237 | 11/1991 | WIPO |
| WO 93/10755 | 6/1993 | WIPO |
| WO 94/05255 | 3/1994 | WIPO |
| WO 94/05279 | 3/1994 | WIPO |
| WO 94/05302 | 3/1994 | WIPO |
| WO 94/09755 | 5/1994 | WIPO |
| WO 95/00136 | 1/1995 | WIPO |
| WO95/13048 | 5/1995 | WIPO |

OTHER PUBLICATIONS

Merck Index, 11th Ed., p. 79 (Merck).

J. Of The American College of Toxicology, vol. 10, No. 1, pp. 33–52, 1991.

Primary Examiner—Phyllis G. Spivack
Attorney, Agent, or Firm—Loretta J. Henderson; John M. Howell; David L. Suter

[57] ABSTRACT

The subject invention relates to desquamation compositions comprising a combination of sulfhydryl compounds and zwitterionic surfactants. The subject invention further relates to methods of desquamation in mammalian skin and treating acne in mammalian skin.

25 Claims, No Drawings

DESQUAMATION COMPOSITIONS

This is a continuation-in-part of application Ser. No. 08/558,944, filed on Nov. 13, 1995, allowed Jan. 7, 1997, which is a file-wrapper-continuation of application Ser. No. 08/209,041, filed on Mar. 9, 1994, abandoned, which is a continuation-in-part of application Ser. No. 08/150,942, filed on Nov. 12, 1993, abandoned.

TECHNICAL FIELD

The subject invention relates to the field of skin conditioning. Specifically, the subject invention relates to methods for improving the suppleness or smoothness of skin by removing scales from the skin surface.

BACKGROUND

Skin is composed of two layers: the epidermis (or cuticle) and the dermis. The epidermis is a thin outer layer composed of stratified epithelium. The outermost layer of the epidermis is the stratum corneum which is composed of keratin protein-filled, flattened cells surrounded by thin lipid layers. The cells are believed to be attached to one another by protein connections (desmosomes) between cells. The cells in the deepest portion of the epidermis, the basal layer, multiply and grow, pushing the older cells of the epidermis upward and toward the surface. As these cells move upward they become flattened. The epidermis is generally devoid of blood vessels and depends on blood vessels found in the dermis for nutrition. The more superficial cells of the epidermis, being far removed from the nutrient supply, gradually differentiate, transforming their proteins into keratin. This process of keratinization results in the death of the cells. Keratin is an insoluble proteinaceous material and gives the stratum corneum a horn-like consistency. The outermost dead stratum corneum cells are gradually shed and replaced by more recently keratinized cells.

In normal skin, the stratum corneum is shed as individual cells or as small clusters of cells. Skin problems such as dry skin, psoriasis, ichthytosis, dandruff, acne, callus, photo-damaged skin, aged skin, and sunburn can be described as disorders of keratinization in which the shedding of stratum corneum cells at the skin surface is altered relative to normal, young, healthy skin. Such alteration results in large clusters of cells leading to visible scaling of the skin, a build-up of keratinaceous material on the surface or in follicles or ducts and/or a rough texture to the skin surface. These aforementioned skin problems are known to be improved by removal of the outermost keratinaceous material.

For the foregoing reasons, there is a need for an efficacious agent for removing surface scales from the stratum corneum of mammalian skin.

It is an object of the subject invention to provide topical compositions for desquamation (scale removal) from the stratum corneum of mammalian skin.

It is a further object of the subject invention to provide such compositions which are gentler and less irritating to the skin than existing compositions.

It is also an object of the subject invention to provide methods for removal of scales in mammalian skin.

SUMMARY

The subject invention involves a combination of:
(a) one or more sulfhydryl compound(s) selected fore the group consisting of N-acetyl-L-cysteine, methionine, glutathione, dithiothreitol, dithioerythritol, homocysteine, and cosmetically- and/or pharmaceutically-acceptable salts thereof; and
(b) one or more zwitterionic surfactant(s) having the structure:

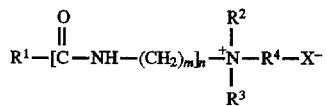

wherein
(a) $R^1$ is unsubstituted, saturated or unsaturated, straight or branched chain alkyl having from about 9 to about 22 carbon atoms;
(b) m is an integer from 1 to 3;
(c) n is 0 or 1;
(d) $R^2$ and $R^3$ are, independently, alkyl having from 1 to about 3 carbon atoms, unsubstituted or mono-substituted with hydroxy;
(e) $R^4$ is saturated or unsaturated, straight or branched chain alkyl, which is unsubstituted or mono-substituted with hydroxy, having from 1 to about 5 carbon atoms; and
(f) X is $CO_2$, $SO_3$ or $SO_4$.

Such a combination and compositions comprising it satisfy the need for an efficacious, easily administered agent for desquamation of skin, having little or no undesirable side effects. The subject invention is also directed to a method of removing scales in a mammal susceptible to or suffering from abnormal keratinization, comprising application of a composition of the subject invention. The subject invention is further directed to a method of treating acne in a mammal susceptible to or suffering from acne.

The compositions of the subject invention comprise a safe and effective amount of the sulfhydryl compound in combination with a safe and effective amount of the zwitterionic surfactant, and a cosmetically- and/or pharmaceutically-acceptable carrier.

These and other features, aspects and advantages of the subject invention will become better understood with reference to the following description and appended claims.

DETAILED DESCRIPTION OF THE INVENTION

It has been unexpectedly found that a combination of certain sulfhydryl compounds and certain zwitterionic surfactants exhibits the ability to remove scales from the stratum corneum in mammalian skin and scalp, without undesirable side effects. While the subject invention is not limited to any particular mode of action, it is believed that the subject combination works by affecting the skin surface's proteolytic enzyme which degrades the protein connections (desmosomes) between cells, thus causing cell or scale shedding. The subject invention thus activates the skin's natural desquamation process at the surface of problem skin.

As used herein "desquamation" means the shedding or removal of scales from the outermost layer (stratum corneum) of the epidermis.

As used herein "treating ache" means preventing, retarding and/or arresting the process of ache formation in mammalian skin.

As used herein, the term "alkyl", unless otherwise indicated, means carbon-containing chains, (i.e., hydrocarbon chains), which may be straight or branched, substituted or unsubstituted, saturated or unsaturated. Preferred alkyl are saturated, straight chain and unsubstituted.

As used herein "sulfhydryl compound" means a compound which contains an S—H group and which is capable of donating a hydrogen atom selected from the group consisting of:

a) N-acetyl-L-cysteine, having the structure:

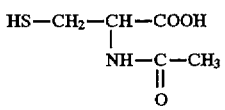

b) glutathione, having the structure:

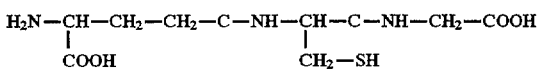

c) dithiothreitol, having the structure:

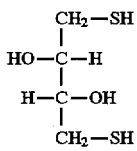

d) dithioerythritol, having the structure:

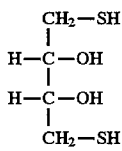

e) homocysteine, having the structure:

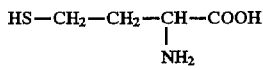

and f) cosmetically- and/or pharmaceutically-acceptable salts of the foregoing compounds.

The compositions may include one or more of the sulfhydryl compounds. "Sulfhydryl compound" is meant to include cosmetically- and/or pharmaceutically-acceptable salts of the foregoing sulfhydryl compounds. Cosmetically- and/or pharmaceutically-acceptable salts of the sulfhydryl compound include, but are not limited to alkali metal salts, e.g., sodium, lithium, potassium and rubidium salts; alkaline earth metal salts, e.g., magnesium, calcium and strontium salts; non-toxic heavy metal salts, e.g., aluminum, and zinc salts; boron salts; silicon salts; ammonium salts; trialkylammonium salts, e.g., trimethylammonium and triethylammonium; and tetralkylonium salts. Preferred cosmetically- and/or pharmaceutically-acceptable salts of the sulfhydryl compound include $Na^+$, $K^+$, $Ca^{++}$, $Mg^{++}$, $Al_2(OH)_5^+$, $NH_4^+$, $(HOCH_2CH_2)_3NH^+$, $(CH_3CH_2)_3NH^+$, $(CH_3CH_2)_4N^+$, $C_{12}H_{25}(CH_3)_3N^+$ and $C_{12}H_{25}(C_5H_4N)_3N^+$ salts. More preferred salts of the sulfhydryl compound include $Na^+$, $K^+$, $NH_4^+$, and $(HOCH_2CH_2)_3NH^+$ salts. Most preferred salts of the sulfhydryl compound include $Na^+$ and $NH_4^+$ salts. Suitable salts of the sulfhydryl compound are described, for example, in U.S. Pat. No. 5,296,500, issued to Hillebrand on Mar. 22, 1994, incorporated herein by reference.

Preferred sulfhydryl compounds useful in the subject invention include N-acetyl-L-cysteine, glutathione, dithiothreitol, dithioerythritol, cosmetically- and/or pharmaceutically-acceptable salts of the foregoing compounds, and mixtures of any of the foregoing. The most preferred sulfhydryl compound is N-acetyl-L-cysteine or a cosmetically- and/or pharmaceutically-acceptable salt thereof.

As used herein "zwitterionic surfactant" means a compound having the structure:

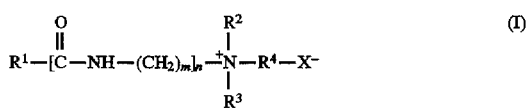

In structure (I) $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about carbon atoms; more preferably still from about 14 to about 16 carbon atoms.

In structure (I), m is an integer from 1 to 3, preferably 2 or 3; more preferably 3.

In structure (I), n is either 0 or 1; n is preferably 0.

In structure (I), $R^2$ and $R^3$ are, independently, selected from the group consisting of alkyl having from 1 to about 3 carbon atoms, unsubstituted or mono-substituted with hydroxy. Preferred $R^2$ and $R^3$ are $CH_3$.

In structure (I), X is selected from the group consisting of $CO_2$, $SO_3$ and $SO_4$.

In structure (I), $R^4$ is selected from the group consisting of saturated or unsaturated, straight or branched chain alkyl, unsubstituted or mono-substituted with hydroxy, having from 1 to about 5 carbon atoms. When $X=CO_2$, $R^4$ preferably has 1 or 3 carbon atoms, more preferably 1 carbon atom. When $X=SO_3$ or $SO_4$, $R^4$ preferably has from about 2 to about 4 carbon atoms, more preferably 3 carbon atoms.

Preferred zwitterionic surfactants of the subject invention include the following compounds:

a) cetyl betaine, having the structure:

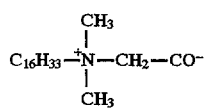

b) stearyl betaine, having the structure:

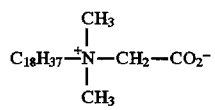

c) cocoamidopropylbetaine, having the structure:

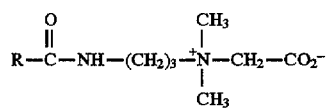

wherein R is unsubstituted, saturated, straight chained alkyl with from about 9 to about 13 carbon atoms;

d) cetyl propyl hydroxy sultaine, having the structure:

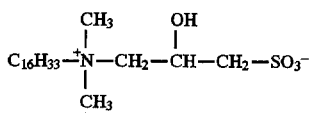

e) cocoamidopropyl hydroxy sultaine, having the structure:

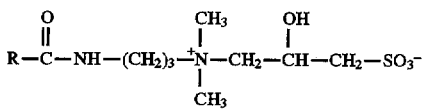

wherein R has from about 9 to about 13 carbon atoms; and
f) behenyl betaine, having the structure:

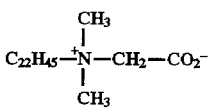

One or more zwitterionic surfactants may be used in the present invention. More preferred zwitterionic surfactants of the subject invention include cetyl betaine, stearyl betaine, cocoamidopropyl betaine, cetyl propyl hydroxy sultaine or mixtures thereof. Still more preferred zwitterionic surfactants of the subject invention include cetyl betaine, stearyl betaine, cocoamidopropyl betaine or mixtures thereof. The zwitterionic surfactant is even more preferably cetyl betaine and/or stearyl betaine. The most preferred zwitterionic surfactant of the subject invention is cetyl betaine.

"Zwitterionic surfactant" is meant to include cosmetically- and/or pharmaceutically-acceptable salts of the foregoing compounds. Preferred cosmetically- and/or pharmaceutically-acceptable salts include alkali metal salts, alkaline earth metal salts, non-toxic heavy metal salts, boron salts, silicon salts, ammonium salts, trialkylammonium salts, and tetralkylammonium salts such as described hereinabove in reference to the sulfyhydryl compound.

As used herein "topical application" means directly laying on or spreading on outer skin.

As used herein, "safe and effective mount" means a sufficient amount of a compound, composition or other material described by this phrase to significantly induce a positive modification in the condition being treated, but low enough to avoid serious side effects (at a reasonable benefit/risk ratio), within the scope of sound medical judgment. The safe and effective amount of the compound, composition or other material will vary with the particular condition being treated, the age and physical condition of the patient being treated, the severity of the condition, the duration of the treatment, the nature of concurrent therapy, the specific compound, composition or other material employed, the particular cosmetically- and/or pharmaceutically-acceptable carrier utilized, and like factors within the knowledge and expertise of the attending physician.

As used herein "comprising" means that other steps and ingredients which do not affect the end result can be added. This term encompasses the terms "consisting of" and "consisting essentially of".

As used herein, "cosmetically- and/or pharmaceutically-acceptable" means that the salts, drugs, medicaments, inert ingredients or other materials which the phrase describes are suitable for use in contact with the tissues of humans and lower animals without undue toxicity, incompatibility, instability, irritation, allergic response and the like, commensurate with a reasonable benefit/risk ratio.

As used herein, "primary actives," and "primary active agents" means a combination of at least one of the sulfhydryl compounds and at least one of the zwitterionic surfactants according to structure (I) described herein above.

The compositions of the present invention comprise at least one of the sulfhydryl compounds and at least one of the zwitterionic surfactants according to structure (I) described herein above in amounts that are safe and effective for causing desquamation. The compositions preferably comprise from about 0.1% to about 20%, more preferably from about 0.2% to about 10%, also preferably about 0.5% to about 5% of the sulfhydryl compound, and from about 0.1% to about 10%, more preferably from about 0.2% to about 5%, also preferably from about 0.5% to about 2% of zwitterionic surfactant according to structure (I).

Cosmetically- and/or Pharmaceutically-Acceptable Carrier

The compositions of the subject invention are administered topically to a biological subject, i.e., by the direct laying on or spreading of the composition on the skin of the subject. The topical compositions of this invention involve compositions suitable for topical application to mammalian skin, the composition comprising a safe and effective amount of the primary active agents and a cosmetically- and/or pharmaceutically-acceptable topical carrier.

The phrase "cosmetically- and/or pharmaceutically-acceptable carrier", as used herein, means one or more compatible solid or liquid filler diluents which are suitable for administration to a human or lower animal. The term "compatible", as used herein, means that the components of the compositions of this invention are capable of being comingled with the primary actives of the present invention, and with each other, in a manner such that there is no interaction which would substantially reduce the efficacy of the composition under ordinary use situations. Cosmetically- and/or pharmaceutically-acceptable carriers must, of course, be of sufficiently high purity and sufficiently low toxicity to render them suitable for administration to the human or lower animal being treated.

The topical compositions useful in the subject invention may be made into a wide variety of product types. These include, but are not limited to, lotions, creams, gels, sticks, sprays, ointments, pastes, mousses and cosmetics. These product types may comprise several types of carrier systems including, but not limited to, solutions, emulsions, gels, solids, and liposomes.

The topical compositions useful in the subject invention formulated as solutions typically include a cosmetically- and/or pharmaceutically-acceptable aqueous or organic solvent. The phrase "cosmetically- and/or pharmaceutically-acceptable organic solvent" refers to a solvent which is capable of having the primary actives dispersed or dissolved therein, and of possessing acceptable safety properties (e.g., irritation and sensitization characteristics). Water is a preferred solvent. Examples of suitable organic solvents include: propylene glycol, polyethylene glycol (Molecular Weight 200–600 g/mole), polypropylene glycol (Molecular Weight 425–2025 g/mole), glycerol, 1,2,4-butanetriol, sorbitol esters, 1,2,6-hexanetriol, ethanol, isopropanol, sorbitol esters, butanediol, and mixtures thereof. These solutions useful in the subject invention preferably contain from about 80% to about 99.99% of an acceptable aqueous or organic solvent.

If the topical compositions useful in the subject invention are formulated as an aerosol and applied to the skin as a spray-on, a propellant is added to a solution composition. Examples include chloro-fluorinated lower molecular weight hydrocarbons. A more complete disclosure of propellants useful herein can be found in Sagarin, *Cosmetics Science and Technology*, 2nd Edition, Vol. 2, pp. 443–465 (1972)

Topical compositions useful in the subject invention may be formulated as a solution comprising an emollient. Such compositions preferably contain from about 2% to about 50% of a topical cosmetically- and/or pharmaceutically-acceptable emollient.

As used herein, "emollients" refer to materials used for the prevention or relief of dryness, as well as for the protection of the skin. A wide variety of suitable emollients are known and may be used herein. Sagarin, *Cosmetics, Science and Technology*, 2nd Edition, Vol. 1, pp. 32–43 (1972), incorporated herein by reference, contains numerous examples of suitable materials.

A lotion can be made from a solution carrier system. Lotions typically comprise from about 1% to about 20%, preferably from about 5% to about 10%, of an emollient; and from about 50% to about 90%, preferably from about 60% to about 80%, water.

Another type of product that may be formulated from a solution carrier system is a cream. A cream typically comprises from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may comprise from about 2% to about 10% of an emollient; and from about 0.1% to about 2% of a thickening agent. A more complete disclosure of thickening agents useful herein can be found in Sagarin, *Cosmetics, Science and Technology*, 2nd Edition, Vol. 1, pp. 72–73 (1972).

If the carrier is formulated as an emulsion, preferably from about 1% to about 10%, more preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dickert et at.; U.S. Pat. No. 4,421,769, issued Dec. 20, 1983, Dixon et al.; and McCutcheon's *Detergents and Emulsifiers*, North American Edition, pages 317–324 (1986).

Preferred emulsions have a low viscosity (viscosities of about 50 centistokes or less). More preferred emulsions have viscosities of about 10 centistokes or less. Even more preferred emulsions have viscosities of about 5 centistokes or less. High molecular weight silicones may be used in such emulsions. When used, such silicones should be used in an amount which does not substantially decrease the efficacy of the zwitterionic surfactant. Preferred emulsions are substantially free of high molecular weight silicones. In such emulsions, anti-foaming compositions are also preferably added because the absence of silicones, in some compositions, may cause foaming upon application. Preferred emulsions of the subject compositions are substantially free of occlusives, such as petrolatum, which appear to diminish the zwitterionic effect. Preferred emulsions of the subject compositions contain humectants, such as glycerin.

Compositions of this invention useful for cleansing preferably contain from about 1% to about 90%, more preferably from about 5% to about 10%, of a cosmetically- and/or pharmaceutically acceptable surfactant.

The physical form of the cleansing compositions is not critical. The compositions can be, for example, formulated as toilet bars, liquids, shampoos, pastes, or mousses. Toilet bars are most preferred since this is the form of cleansing agent most commonly used to wash the skin. Rinse-off cleansing compositions, such as shampoos, require a delivery system adequate to deposit sufficient levels of actives on the skin and scalp. A preferred delivery system involves the use of insoluble complexes. For a more complete disclosure, see U.S. Pat. No. 4, 835,148, Barford et al., issued May 30, 1989; incorporated herein by reference in its entirety.

The surfactant component of the cleansing compositions useful in the subject invention are selected from anionic, nonionic, zwitterionic, amphoteric and ampholytic surfactants, as well as mixtures of these surfactants. Such surfactants are well known to those skilled in the detergency art.

The cleansing compositions useful in the subject invention can optionally contain, at their art-established levels, materials which are conventionally used in cleansing compositions. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety, for exemplary surfactants useful herein. Examples of a broad variety of additional surfactants useful herein are described in McCutcheon's, *Detergents and Emulsifiers*, North American Edition (1986), published by Allured Publishing Corporation, which is incorporated herein by reference in its entirety.

The solutions, aerosols, lotions, creams, ointments, emulsions and cleansing compositions comprise a safe and effective amount of sulfhydryl compound, preferably from about 0.1% to about 20%, more preferably from about 0.2% to about 10%, also preferably about 0.5% to about 5% of sulfhydryl compound. Such compositions also comprise a safe and effective amount of zwitterionic surfactant, preferably from about 0.1% to about 10%, more preferably from about 0.2% to about 5%, also preferably from about 0.5% to about 2% of zwitterionic surfactant. Preferred solutions, aerosols, lotions, creams, ointments, emulsions and cleansing compositions more preferably also contain a preservative, preservative enhancer, zinc, and/or a zinc salt as described herein. These agents may be incorporated into the aforementioned formulations in the amounts described herein.

The compositions of the present invention are preferably formulated to have a pH of 7 or below. The pH values of these compositions preferably range from about 2 to about 7, more preferably from about 3 to about 6, most preferably from about 4.5 to about 5.5. Compositions having a pH within the range of about 4.5 to 7 tend to exhibit less skin irritation, less odor, and greater shelf stability relative to corresponding compositions having a pH of greater than about 8.5. Preferred emulsions of the invention are formulated at low pH values, preferably from about 2 to about 4, more preferably about 3.

Other Ingredients

The compositions of this invention may contain other ingredients, including but not limited to preservatives, preservative enhancers, and actives in addition to the primary actives. However, certain agents may decrease the activity of the zwitterionic surfactant and are therefore preferably avoided or if used, used in relatively low levels. For example, free fatty acids, high molecular weight silicones, occlusives such as petrolatum, and thickeners such as salcare and hydroxyethylcellulose may decrease the activity of the zwitterionic surfactant and are therefore preferably not employed in the present compositions. If such agents are employed, they should be used in relatively low levels. In addition, certain agents may decrease the activity of the sulfhydryl compound, particularly N-acetyl-L-cysteine, in topical formulations. First, an excessive number of microbes may decrease the activity of the sulfhydryl compound, for example by microbial metabolism of the compound. Second, it has been found that formaldehyde may chemically react with the sulfhydryl compound to decrease its activity. Thus, when a composition containing the sulfhydryl compound is formulated with a formaldehyde or a formaldehyde forming preservative or other material, the composition may have decreased activity of the sulfhydryl compound over time relative to the corresponding formulation that does not contain formaldehyde or a compound capable of forming formaldehyde. Therefore, it is desirable to provide compositions containing sulfhydryl compounds that have preservative efficacy and which do not include formaldehyde or formaldehyde forming preservatives or other materials.

The compositions of this invention are therefore preferably substantially free of formaldehyde and materials that may form or release formaldehyde when present in the composition, including preservatives that may form or release formaldehyde in the composition. Formaldehyde and materials that may form or release formaldehyde in the composition are alternatively referred to herein as "formaldehyde donor(s)." As used herein, "substantially free of formaldehyde donors" means that there are no detectable formaldehyde donors, preferably no formaldehyde donors. The presence of formaldehyde donors may be indicated by the presence of formaldehyde in the composition by any suitable analytical technique, for example high pressure liquid chromatography. The presence of such donors may be detected initially or evidenced by the generation of formaldehyde over time.

The topical compositions of the invention preferably comprise one or more preservatives. Preferred preservatives are those which are substantially free of formaldehyde donors. Thus, the preservatives preferred for use herein are those that do not form or release formaldehyde in the composition either in the process of preserving or in an unrelated process. In contrast, formaldehyde forming or releasing preservatives form or release formaldehyde in the composition either in the process of preserving or in an unrelated process.

More preferred preservatives include benzyl alcohol, propylparaben, ethylparaben, butylparaben, methylparaben, benzylparaben, isobutylparaben, phenoxyethanol, ethanol, sorbic acid, benzoic acid, methylchloroisothiazolinone, methylisothiazolinone (a preservative containing a mixture of methylchloroisothiazolinone and methylisothiazolinone being commercially available, for example, from Rohm & Haas as Kathon CG®), methyl dibromoglutaronitrile (commercially available, for example, from Calgon as Tektamer 38®), dehydroacetic acid, o-phenylphenol, sodium bisulfite, dichlorophen, salts of any of the foregoing compounds, and mixtures of any of the foregoing compounds.

Even more preferred preservatives are selected from the group consisting of benzyl alcohol, propylparaben, methylparaben, phenoxyethanol, methylchloroisothiazolinone, methylisothiazolinone, benzoic acid, salts of any of the foregoing preservatives, and mixtures of any of the foregoing compounds.

Still more preferred preservatives are benzyl alcohol, propylparaben, methylparaben, phenoxyethanol and mixtures thereof. Yet even more preferably, the preservative is a mixture of propylparaben and methyl paraben with either or both of benzyl alcohol and phenoxyethanol. In addition to stability of the sulfhydryl compound, these mixtures provide broad preservative efficacy with no or only minimal risk of skin irritation to the user. Most preferably, the preservative is a mixture of benzyl alcohol, propylparaben and methylparaben. In addition to stability of the sulfhydryl compound and broad preservative efficacy, this mixture presents a particularly low risk of skin irritation to the user.

The use of the foregoing preservatives that are substantially free of formaldehyde donors is described in more detail in the copending U.S. Patent Application entitled "Topical Compositions Comprising N-Acetyl-L-Cysteine," filed on Jun. 7, 1995 in the names of Greg. G. Hillebrand and Marcia S. Schnicker, which is incorporated herein by reference in its entirety. The foregoing preservatives are preferably used in the compositions of this invention in the same amounts as described for the compositions of the just referenced patent application.

The compositions of this invention preferably comprise a safe and effective mount of a preservative enhancer. As used herein, the term "preservative enhancer" means an agent whose purpose is to enhance the activity of the preservative. As will be understood by the artisan having ordinary skill, the preservative enhancer does not itself typically provide sufficient efficacy; it tends to increase the efficacy of the preservative. Enhancement of the preservative efficacy may involve chelation. Preferred preservative enhancers useful in the present invention include ethylenediaminetetraacetic acid (EDTA), butylene glycol, propylene glycol, ethanol, and mixtures thereof. Where the preservative includes a parsben, e.g., methyl or propyl parsben, EDTA is the preferred preservative enhancer. The use of such enhancers is described in more detail in the above-referenced and incorporated copending U.S. patent application entitled "Topical Compositions Comprising N-Acetyl-L-Cysteine," filed on Jun. 7, 1995 in the names of Greg. G. Hillebrand and Marcia S. Schnicker. The preservative enhancers are preferably used in the compositions of this invention in the same amounts as described for the compositions of the just referenced patent application.

The compositions of the invention preferably contain zinc or a zinc salt which may complex with the sulfhydryl compound. Without being bound by theory, the zinc most likely removes odor by complexing with malodorous $H_2S$ which may be formed in trace amounts as the sulfhydryl compound decomposes. The zinc may additionally or alternatively increase the stability of the sulfhydryl compound. The use of zinc salts in a manner which is suitable for the present invention is further described in U.S. Pat. No. 5,296,500, Hillebrand, issued on Mar. 22, 1994, which is incorporated herein by reference.

The zwitterionic surfactant tends to decrease the viscosity of the composition. Therefore, a thickener may be employed in the compositions of the invention to thicken the composition and/or to minimize the risk of phase separation. The thickener should be compatible with the components of the composition or otherwise be employed in relatively low levels so as to not significantly decrease the efficacy of the zwitterionic surfactant. Exemplary thickeners include hydroxyethylcellulose (e.g., commercially available from Aqualon of Wilmington, Del.) and salcare.

The compositions of the subject invention may optionally comprise other actives capable of functioning in different ways to enhance the benefits of the sulfhydryl and/or zwitterionic surfactant actives (thus, the other actives should not significantly reduce the activity of the sulfhydryl or zwitterionic surfactant compounds). Examples of such substances include, but are not limited to anti-inflammatory agents, antimicrobial agents, anti-androgens, sunscreens, sunblocks, anti-oxidants/radical scavengers, chelators, anti-dandruff agents, and salicylic acid.

A. Anti-Inflammatory Agents

An anti-inflammatory agent may be included as an active along with the primary actives, for better activity. A safe and effective amount of an anti-inflammatory agent may be added to the compositions useful in the subject invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, flucinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, flurandrenolone, fludrocortisone, diflurosone diacetate, flurandrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, reference may be had to standard texts, including *Anti-inflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et at., Academic Press, New York (1974).

Specific non-steroidal anti-inflammatory agents useful in the composition invention include, but are not limited to:

1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and
6) the pyrazoles, such as phenylbutazone, oxyphenbutazone, feprazone, azapropazone, and trimethazone.

Mixtures of these non-steroidal anti-inflammatory agents may also be employed, as well as the cosmetically- and/or pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Finally, so-called "natural" anti-inflammatory agents are useful in methods of the subject invention. For example, candelilla wax, alpha bisabolol, aloe vera, Manjistha (extracted from plants in the genus Rubia, particularly *Rubia Cordifolia*), and Guggal (extracted from plants in the genus Commiphora, particularly *Commiphora Mukul*), may be used.

B. Retinoids

In a preferred desquamatory composition useful in the subject invention, one or more retinoids, preferably retinol or retinoic acid, more preferably retinoic acid, is included as an active along with the primary active agents. The inclusion of a retinoid increases the desquamation benefits of the composition. A safe and effective amount of a retinoid may be added to the compositions useful in the subject invention, preferably from about 0.001% to about 0.5%, more preferably from about 0.01% to about 0.1% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

C. Antimicrobial Agents

In a preferred composition useful in the subject invention, an antimicrobial agent is included as an active along with the primary active agents. The inclusion of an antimicrobial agent increases the desquamation benefits of the composition. As used herein, "antimicrobial agent" means a compound capable of destroying microbes, preventing the development of microbes or preventing the pathogenic action of microbes.

A safe and effective amount of an antimicrobial agent may be added to compositions useful in the subject invention, preferably from about 0.001% to about 5%, more preferably from about 0.01% to about 2%, more preferably still from about 0.05% to about 1% of the compositions. Preferred antimicrobial agents useful in the subject invention are benzoyl peroxide, erythromycin, tetracycline, clindamycin, azelaic acid, and sulfur resorcinol.

D. Antiandrogens

In a preferred composition useful in the subject invention, an antiandrogen is included as an active along with the primary active agents. As used herein, "anti-androgen"

means a compound capable of correcting androgen-related disorders by interfering with the action of androgens at their target organs. The target organ for the subject invention is mammalian skin.

E. Sunscreens and Sunblocks

Exposure to ultraviolet light can result in excessive scaling of the stratum corneum. Therefore, in a preferred composition useful in the subject invention, a sunscreen or sunblock is included as an active along with the primary actives of the subject invention. Suitable sunscreens or sunblocks may be organic or inorganic.

A wide variety of conventional sunscreening agents are suitable for use in combination with the desquamation agents. Sagarin, et at., at Chapter VIII, pages 189 et seq., of *Cosmetics Science and Technology*, disclose numerous suitable agents, incorporated herein by reference. Specific suitable sunscreening agents include, for example: p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); Cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-Hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; [3-(4'-methylbenzylidene bornan-2-one) and 4-isopropyl-di-benzoylmethane.

Of these, 2-ethylhexyl-p-methoxycinnamate, 4,4'-t-butyl methoxydibenzoyl-methane, 2-hydroxy-4-methoxybenzophenone, octylidimethyl-p-aminobenzoic acid, digalloyltrioleate, 2,2-dihydroxy-4-methoxybenzophenone, ethyl-4-(bis(hydroxy-propyl)) aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid and mixtures of these compounds, are preferred.

More preferred sunscreens useful in the compositions useful in the subject invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methylaminobenzoic acid ester with 4-hydroxydibenzoylmethane; 4-N,N-(2-ethylhexyl) methylaminobenzoic acid ester of 2-hydroxy-4-(2-hydroxyethoxy)benzophenone; 4-N,N-(2-ethylhexyl)-methylaminobenzoic acid ester of 4-(2-hydroxyethoxy) dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

Suitable inorganic sunscreens or sunblocks include metal oxides, e.g., zinc oxide and titanium dioxide.

A safe and effective amount of sunscreen may be used as an added active in compositions useful in the subject invention. The sunscreening agent must be compatible with the primary active agents. The composition preferably comprises from about 1% to about 20%, more preferably from about 2% to about 10%, of a sunscreening agent. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

F. Anti-Oxidants/Radical Scavengers

While the sulfhydryl compound (e.g., glutathione) may itself impart anti-oxidant properties to the composition, preferred compositions of the subject invention include an anti-oxidant/radical scavenger as an active in addition to the primary active agents. The anti-oxidants/radical scavenger enhances the desquamation benefits of the subject invention by providing additional protection against UV radiation which can cause increased scaling in the stratum corneum.

A safe and effective amount of an anti-oxidant/radical scavenger may be added to the compositions useful in the subject invention, preferably from about 0.1% to about 10%, more preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox$^R$), gallic acid and its alkyl esters, especially propyl gallate, uric acid and its salts and alkyl esters, sorbic acid and its salts, the ascorbyl esters of fatty acids amines (e.g., N,N-amines (e.g., N,N- diethylhydroxylamine, amino-guanidine), and dihydroxy fumaric acid and its salts may be used. Preferred antioxidant/radical scavengers are selected from tocopherol sorbate and other esters of tocopherol.

G. Chelators

In a preferred desquamatory composition useful in the subject invention, a chelating agent is included as an active along with the primary active agents. As used herein, "chelating agent" means an active agent capable of removing a metal ion from a system by forming a complex so that the metal ion cannot readily participate in or catalyze chemical reactions. The inclusion of a chelating agent increases the desquamation benefits of the composition by providing added protection against UV radiation which can contribute to excessive scaling.

A safe and effective amount of a chelating agent may be added to the compositions useful in the subject invention, preferably from about 0.1% to about 10%, more preferably from about 1% to about 5%, of the composition. Chelators useful in compositions are disclosed in U.S. patent application Ser. No. 619,805, Bissett, Bush & Chatterjee, filed Nov. 27, 1990 (which is a continuation of U.S. patent application Ser. No. 251,910, filed Oct. 4, 1988); U.S. patent application Ser. No. 514,892, Bush & Bissett, filed Apr. 26, 1990; and U.S. patent application Ser. No. 657,847, Bush, Bissett & Chatterice, filed Feb. 25, 1991; all incorporated herein by reference. Preferred chelators useful in compositions of the subject invention are furildioxime and derivatives thereof.

H. Anti-dandruff Actives

In a preferred composition of the subject invention formulated for application to the scalp, an anti-dandruff agent is included as an active along with the primary active agents. Anti-dandruff agents enhance the desquamation benefits of the subject invention by further preventing and treating the effects of flaking on the scalp. A particularly preferred anti-dandruff agent is zinc pyridinethione.

I. Salicylic Acid

In a preferred composition of the subject invention, salicylic acid is included as an active along with the primary active agents. Preferably, the composition comprises from about 0.1% to about 10%, more preferably from about 0.2% to about 5%, also preferably from about 0.5% to about 2% salicylic acid.

A particularly preferred composition of the invention includes the sulfhydryl compound, the zwitterionic compound and salicylic acid, more preferably in the amounts previously described for each of these components. In such compositions the sulfhydryl compound is preferably N-acetyl-L-cysteine (including cosmetically- and/or pharmaceutically-acceptable salts thereof), and the zwitterionic surfactant is preferably cetyl betaine or stearyl betaine, more preferably cetyl betaine (including cosmetically- and/or pharmaceutically-acceptable salts of these compounds).

The compositions of the present invention are generally prepared by conventional methods such as are known in the art of making topical compositions. Such methods typically involve mixing of the ingredients to a relatively uniform state, with or without heating, cooling, application of vacuum, and the like.

For optimum stability of the sulfhydryl compound, the compositions of this invention should be manufactured, packaged and stored in a manner which avoids simple air oxidation of the sulfhydryl compound, which is well known in the art. Thus, exposure of the compositions to air during manufacture, packaging and storage should be minimized.

Delivery Methods for the Topical Compositions

The topical compositions useful for the methods of the instant invention can be delivered from a variety of delivery devices. The following are two nonlimiting examples.

Medicated Cleansing Pads

The compositions useful herein can be incorporated into a medicated cleansing pad. Preferably these pads comprise from about 50% to about 75% by weight of one or more layers of nonwoven fabric material and from about 20% to about 50% by weight of a liquid composition deliverable from the nonwoven fabric material comprising hydroxy acid comprising salicylic acid and a subject zwitterionic surfactant, or mixture of such surfactants. These pads are described in detail in U.S. Pat. No. 4,891,228, to Thaman et at., issued Jan. 2, 1990; and U.S. Pat. No. 4,891,227, to Thatnan et at., issued Jan. 2, 1990; both of which are incorporated by reference herein in their entirety.

Dispensing Devices

The compositions useful herein can also be incorporated into and delivered from a soft-tipped or flexible dispensing device. These devices are useful for the controlled delivery of the compositions to the skin surface and have the advantage that the treatment composition itself never need be directly handled by the user. Nonlimiting examples of these devices comprise a fluid container including a mouth, an applicator, means for holding the applicator in the mouth of the container, and a normally closed pressure-responsive valve for permitting the flow of fluid from the container to the applicator upon the application of pressure to the valve. The fluid comprises hydroxy acid comprising salicylic acid and a subject zwitterionic surfactant, or mixture of such surfactants.

The valve can include a diaphragm formed from an elastically fluid impermeable material with a plurality of non-intersecting arcuate slits therein, where each slit has a base which is intersected by at least one other slit, and where each slit is out of intersecting relation with its own base, and wherein there is a means for disposing the valve in the container inside of the applicator. Examples of these applicator devices are described in U.S. Pat. No. 4,693,623, to Schwartzman, issued Sep. 15, 1987; U.S. Pat. No. 4,620, 648, to Schwartzman, issued Sep. 15, 1987; U.S. Pat. No. 3,669,323, to Harker et al., issued Jun. 13, 1972; U.S. Pat. No. 3,418,055, to Schwartzman, issued Dec. 24, 1968; and U.S. Pat. No. 3,410,645, to Schwartzman, issued Nov. 12, 1968; all of which are incorporated herein by reference in their entirety. Examples of applicators useful herein are commercially available from Dab-O-Matie, Mount Vernon, N.Y.

Methods For Desquamation and Treatment of Acne

The subject invention relates to methods of removing scales from the stratum corneum of mammals. Such methods comprise topically applying to the skin or scalp an effective amount of the compositions of the subject invention. The term "effective amount", as used herein, means an amount sufficient to provide a scale removal benefit. The composition can be applied for several days, weeks, months or years at appropriate intervals: from about three times a day to about once every three days, preferably from about twice a day to once every other day, also preferably about once a day until satisfactory desquamation has been achieved.

The subject compositions may also be used for one or more of the following: reducing the appearance of large pores, reducing imperfections and/or blemishes in skin color, relieving dryness, eliminating dry rough spots, improving the skin's ability to retain moisture and/or protect itself from environmental stresses, reducing the appearance of fine lines and wrinkles, improving appearance and skin tone, increasing skin firmness and/or suppleness, increasing skin glow and clarity, and/or increasing the skin renewal process.

Typically, in each application, an effective coating of the skin or scalp is achieved by applying from about 0.004 mg/cm$^2$ to about 0.1 mg/cm$^2$ each of one or more of the sulfhydryl compounds and one or more of the zwitterionic surfactants, more preferably from about 0.02 mg/cm$^2$ to about 0.06 mg/cm$^2$, also preferably about 0.04 mg/cm$^2$ of each of these materials.

EXAMPLES

The following examples further describe and demonstrate embodiments within the scope of the subject invention. The examples are given solely for the purpose of illustration and are not to be construed as limitations of the subject invention, as many variations thereof are possible without departing from the spirit and scope of the invention.

Example I

A topical composition is prepared by combining the following components utilizing conventional mixing techniques.

| Ingredient | % Weight |
| --- | --- |
| Water | q.s. |
| Triethanolamine | 0.66 |
| Cetyl Betaine | 6.66 |
| Disodium EDTA | 0.01 |
| Ethanol (95%) | 40.00 |
| N-acetyl-L-cysteine | 2.00 |

The above composition is applied to the face to remove scales at a dose enough to deposit 2 mg of the composition per cm$^2$ skin, once a day. As desquamation progresses, application is reduced to once very other day.

Example II

A cleaning composition is prepared by combining the following ingredients, using conventional mixing techniques:

| Ingredient | % Weight |
| --- | --- |
| Water | q.s. |
| Tetrasodium EDTA | 0.12 |
| Cetyl Betaine | 3.33 |
| Sodium methyl cocoyl taurate | 41.67 |
| Cocoamidopropyl hydroxysultaine | 6.00 |
| Salicylic Acid | 2.00 |
| Cocoamidopropyl betaine | 1.43 |
| Hydroxypropyl methylcellulose | 0.50 |
| Glutathione | 2.00 |
| Perfume | 0.12 |

The cleaning composition is applied to the face twice a day to treat acne. An amount enough to deposit 3 mg of the composition per cm$^2$ skin is used. As existant acne subsides, frequency is reduced to once a day.

Example III

The following hair tonic is prepared by mixing the ingredients according to conventional mixing techniques:

| Ingredient | % Weight |
| --- | --- |
| Triethanolamine lauryl sulfate | 17.0 |
| Coconut.diethanol amide | 2.0 |
| Hydroxypropyl methyl cellulose[1] | 0.2 |
| Corn syrup (80% solids)[2] | 30.0 |
| Dimethylpolysiloxane | 1.0 |
| Cationic cellulose[3] | 0.5 |
| Ethyl alcohol (SDA 40) | 9.0 |
| Vinyl carboxy polymer[4] | 0.7 |
| Methionine | 1.5 |
| Cocoamidopropyl Betaine | 3.5 |
| Perfume, color, preservative | 1.0 |
| Water | q.s. |

Acid or base to pH 6.5
[1]Methocel E4M (Dow Chemical)
[2]42 Dextrose equivalent (Staley 1300)
[3]Polymer JR 400
[4]Carbopol 941 (BF Goodrich)

The composition is applied to the scalp every other day to treat dandruff. A dose of 5 mg of the composition per cm$^2$ skin is applied and then washed off.

Example IV

The following topical gel is prepared by mixing the ingredients according to conventional mixing techniques:

| Ingredients | % Weight |
| --- | --- |
| Alcohol SD-40 (95%) | 40.00 |
| Homocysteine | 2.00 |
| Disodium EDTA | 0.005 |
| Cetyl Betaine | 6.66 |
| Water | q.s. |

The gel is applied to the face at a dose of 0.2 mg composition per cm$^2$ skin three times a day to remove scales. As desquamation progresses, application may be reduced to once a day.

Example V

The following lotion is prepared by mixing the ingredients according to conventional mixing techniques:

| Ingredient | % Weight |
| --- | --- |
| Water | q.s |
| Glycerin | 10.0 |
| Petrolatum | 2.5 |
| Cetyl Alcohol | 1.8 |
| Cyclomethicone and Dimethicone Copolyol | 1.5 |
| Stearyl Alcohol | 1.2 |
| Isopropyl Palmitate | 1.0 |
| Dimethicone | 0.5 |
| Sodium Hydroxide | 0.34 |
| Lanolin Acid | 0.25 |
| Polyethyleneglycol-100 Stearate | 0.25 |
| Stearic Acid | 0.25 |
| Methylparaben | 0.2 |
| Titanium Dioxide | 0.15 |
| EDTA | 0.1 |
| N-acetyl-L-cysteine | 12.0 |
| Cocoamidopropyl Betaine | 5.0 |

The above lotion is applied to the hands once a day at a dose of 0.75 mg composition per cm$^2$ skin. As desquamation progresses, frequency of application may be reduced to once every two days.

Example VI

The following emulsion is prepared by mixing the following ingredients according to conventional mixing techniques:

| Ingredient | % Weight |
| --- | --- |
| Water | q.s. |
| PPG-14 Butyl Ether | 8.0 |
| Cetyl Betaine | 2.0 |
| Glycerin | 4.0 |
| N-acetyl-L-cysteine | 10.0 |
| Stearyl Alcohol | 1.5 |
| Salcare SC 95 | 1.5 |
| Cetyl Alcohol | 1.5 |
| Dimethicone | 1.0 |
| Silica (DC Antifoam) | 0.5 |
| Steareth-21 | 0.45 |
| Steareth-2 | 0.05 |
| Tetrasodium EDTA | 0.02 |

The above lotion is applied to the face once a day at a dose of 0.60 mg composition per $cm^2$ skin. As desquamation progresses, frequency of application may be reduced to once every two days.

Example VII

A skin cream is prepared from the following components.

| Ingredient | Phase code | Weight % in product |
| --- | --- | --- |
| Sterile Water | A | 54.53 |
| Disodium EDTA | A | 0.050 |
| Methyl Paraben | A | 0.150 |
| Glycerin | A | 3.00 |
| Natrasol 330 Plus (modified hydroxy ethyl cellulose from Aqualon) | A | 0.200 |
| polypropylene glycol-15 stearyl ether | B | 3.250 |
| Propyl Paraben | B | 0.100 |
| Cetyl Alcohol | B | 0.559 |
| Stearyl Alcohol | B | 2.028 |
| Behenyl Alcohol | B | 0.221 |
| Steareth-21 | B | 0.366 |
| Steareth-2 | B | 1.097 |
| Distearyldimonium chloride | B | 0.950 |
| N-acetyl-Cysteine | C | 2.00 |
| Zinc Oxide | C | 0.40 |
| Phytic Acid | C | 5.00 |
| Cetyl Betaine | C | 1.50 |
| Methyl Paraben | C | 0.10 |
| Disodium EDTA | C | 0.05 |
| 1M NaOH | C | adjust pH |
| Sterile Water | C | 20.999 |
| DC Q2-1401 (cyclomethicone/dimethiconol-50/50 blend) | D | 0.750 |
| polyethylene Low Density Beads | D | 2.00 |
| Benzyl Alcohol | D | 0.50 |
| Fragrance | D | 0.2 |

The A, B, C, and D phase components are blended separately with a mixer. The A phase and B phase mixtures are separately heated with stirring to 65-70° C. and then combined and blended with a mixer and then homogenized. The A phase plus B phase mixture is allowed to cool to 45-50° C. The C phase mixture is brought to pH 6. The C phase and D phase mixtures are then added to the A phase plus B phase mixture and blended with a mixer. The final pH is adjusted to 6.5.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A topical composition for desquamation in mammalian skin, comprising:
  a) desquamation actives comprising:
     (i) a safe and effective amount of a zwitterionic surfactant having the structure:

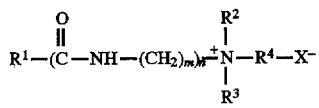

wherein $R^1$ is unsubstituted, saturated or unsaturated, straight or branched chain alkyl having from about 9 to about 22 carbon atoms; m is an integer from 1 to 3; n is 0 or 1; $R^2$ and $R^3$ are, independently, alkyl having from 1 to about 3 carbon atoms, unsubstituted or mono-substituted with hydroxy; $R^4$ is saturated or unsaturated, straight or branched chain alkyl, unsubstituted or mono-substituted with hydroxy, having from 1 to about 5 carbon atoms; and X is selected from the group consisting of $CO_2$, $SO_3$ and $SO_4$; cosmetically- and/or pharmaceutically-acceptable salts of the foregoing compounds; and combinations thereof: and
     (ii) a safe and effective amount of a sulfhydryl compound selected from the group consisting of N-acetyl-L-cysteine, glutathione, dithiothreitol, dithioerythritol, homocysteine, cosmetically-and/or pharmaceutically-acceptable salts of any of the foregoing compounds, and combinations thereof; and
  b) a cosmetically- and/or pharmaceutically-acceptable topical carrier.

2. The composition of claim 1 wherein the sulfhydryl compound is selected from the group consisting of N-acetyl-L-cysteine, glutathione, cosmetically-and/or pharmaceutically-acceptable salts of any of the foregoing compounds, and combinations thereof.

3. The composition of claim 2 wherein the composition further comprises from about 0.1% to about 10% salicylic acid.

4. The composition of claim 2 wherein:
  (a) $R^2$ and $R^3$ are selected from the group consisting of $CH_3$, $CH_2CH_2OH$ and $CH_2CH_2CH_2OH$;
  (b) X is $CO_2$ or $SO_3$; and
  (c) m is 2 or 3.

5. The composition of claim 4 wherein $R^4$ has from 1 to about 3 carbon atoms when X is $CO_2$, and $R^4$ has from about 2 to about 4 carbon atoms when X is $SO_3$.

6. The composition of claim 5 wherein the zwitterionic surfactant is behenyl betaine.

7. The composition of claim 5 wherein:
  a) $R^1$ has from about 11 to about 18 carbon atoms;
  b) $R^2$ and $R^3$ are $CH_3$; and
  c) $R^4$ has 1 carbon atom when X is $CO_2$; and $R^4$ has 3 carbon atoms when X is $SO_3$.

8. The composition of claim 7 wherein:
  (a) $R^4$ has 3 carbon atoms;
  (b) X is $SO_3$;
  (c) m is 3; and
  (d) n is 1.

9. The composition of claim 7 wherein the sulfhydryl compound is N-acetyl-L-cysteine, a cosmetically- and/or pharmaceutically-acceptable salt of N-acetyl-L-cysteine, or a combination thereof.

10. The composition of claim 9 wherein the zwitterionic surfactant is cocoamidopropyl betaine or cetyl propyl hydroxy sultaine.

11. The composition of claim 9 wherein the zwitterionic surfactant is cetyl betaine.

12. The composition of claim 9 wherein the zwitterionic surfactant is stearyl betaine.

13. The composition of claim 7 wherein:

(a) $R^4$ has 1 carbon atom;

(b) X is $CO_2$;

(c) m is 3; and (d) n is 1.

14. The topical composition of claim 1 wherein said desquamation actives consist essentially of said zwitterionic surfactant and said sulfhydryl compound.

15. A topical composition comprising:

(a) from about 0.1% to about 10% of a zwitterionic surfactant having the structure:

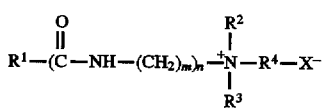

wherein $R^1$ is unsubstituted, saturated or unsaturated, straight or branched chain alkyl having from about 9 to about 22 carbon atoms; m is an integer from 1 to 3; n is 0 or 1; $R^2$ and $R^3$ are, independently, alkyl having from 1 to about 3 carbon atoms, unsubstituted or mono-substituted with hydroxy; $R^4$ is saturated or unsaturated, straight or branched chain alkyl, unsubstituted or mono-substituted with hydroxy, having from 1 to about 5 carbon atoms; and X is selected from the group consisting of $CO_2$, $SO_3$ and $SO_4$; cosmetically- and/or pharmaceutically-acceptable salts of the foregoing compounds; and combinations thereof;

(b) from about 0.1% to about 20% of a sulfhydryl compound selected from the group consisting of N-acetyl-L-cysteine, glutathione, dithiothreitol, dithioerythritol, homocysteine, cosmetically- and/or pharmaceutically-acceptable salts of any of the foregoing compounds, and combinations thereof; and (c) a cosmetically- and/or pharmaceutically-acceptable topical carrier.

16. The topical composition of claim 15 comprising from about 0.5% to about 5% of said sulfhydryl compound and from about 0.5% to about 2% of said zwitterionic surfactant.

17. A method of achieving desquamation of mammalian skin comprising topically applying to a mammal in need of such treatment a composition comprising:

a) a safe and effective amount of a sulfhydryl compound selected from the group consisting of N-acetyl-L-cysteine, glutathione, dithiothreitol, dithioerythritol, homocysteine, cosmetically- and/or pharmaceutically-acceptable salts of any of the foregoing compounds, and combinations thereof; and b) a safe and effective amount of a zwitterionic surfactant having the structure:

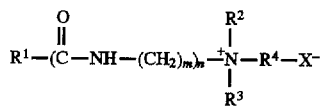

wherein $R^1$ is unsubstituted, saturated or unsaturated, straight or branched chain alkyl having from about 9 to about 22 carbon atoms; m is an integer from 1 to 3; n is 0 or 1; $R^2$ and $R^3$ are, independently, alkyl having from 1 to about carbon atoms, unsubstituted or mono-substituted with hydroxy; $R^4$ is saturated or unsaturated, straight or branched chain alkyl, unsubstituted or mono-substituted with hydroxy, having from 1 to about 5 carbon atoms; and X is selected from the group consisting of, $CO_2$, $SO_3$ and $SO_4$; cosmetically- and/or pharmaceutically-acceptable salts of the foregoing compounds, and combinations thereof; and (c) a cosmetically- and/or pharmaceutically-acceptable topical carrier.

18. The method of claim 17 wherein:

(a) $R^2$ and $R^3$ are selected from the group consisting of $CH_3$, $CH_2CH_2OH$ and $CH_2CH_2CH_2OH$;

(b) X is $CO_2$ or $SO_3$;

(c) m is 2 or 3; and (d) the sulfhydryl compound is selected from the group consisting of N-acetyl-L-cysteine, glutathione, cosmetically- and/or pharmaceutically-acceptable salts of any of the foregoing compounds, and combinations thereof.

19. The method of claim 18 wherein:

(a) the amount of sulfhydryl compound applied is from about 0.004 $mg/cm^2$ skin to about 0.1 $mg/cm^2$ skin; and (b) the amount of zwitterionic surfactant applied is from about 0.004 $mg/cm^2$ skin to about 0.1 $mg/cm^2$ skin.

20. The method of claim 19 wherein:

(a) the amount of sulfhydryl compound applied is from about 0.02 $mg/cm^2$ skin to about 0.06 $mg/cm^2$ skin; and (b) the amount of zwitterionic surfactant applied is from about 0.02 $mg/cm^2$ skin to about 0.06 $mg/cm^2$ skin.

21. The method of claim 20 wherein;

(a) the zwitterionic surfactant is stearyl betaine; and (b) the sulfhydryl compound is N-acetyl-L-cysteine, a cosmetically- and/or pharmaceutically-acceptable salt of N-acetyl-L-cysteine, or a combination thereof.

22. The method of claim 20 wherein;

(a) the zwitterionic surfactant is cetyl betaine; and (b) the sulfhydryl compound is N-acetyl-L-cysteine, a cosmetically- and/or pharmaceutically-acceptable salt of N-acetyl-L-cysteine, or a combination thereof.

23. A method of treating acne in mammalian skin comprising topically applying to a mammal susceptible to or suffering from ache a composition comprising:

a) a safe and effective amount of a sulfhydryl compound selected from the group consisting of N-acetyl-L-cysteine, glutathione, dithiothreitol, dithioerythritol, homocysteine, cosmetically- and/or pharmaceutically-acceptable salts of any of the foregoing compounds, and combinations thereof; and b) a safe and effective amount of a zwitterionic surfactant having the structure:

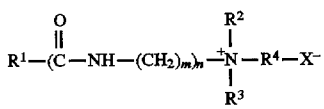

wherein $R^1$ is unsubstituted, saturated or unsaturated, straight or branched chain alkyl having from about 9 to about 22 carbon atoms; m is an integer from 1 to 3; n is 0 or 1; $R^2$ and $R^3$ are, independently, alkyl having from 1 to about 3 carbon atoms, unsubstituted or mono-substituted with hydroxy; $R^4$ is saturated or unsaturated, straight or branched chain alkyl, unsubstituted or mono-substituted with hydroxy, having from 1 to about 5 carbon atoms; and X is selected from the group consisting of $CO_2$, $SO_3$ and $SO_4$; cosmetically- and/or pharmaceutically-acceptable salts of the foregoing compounds, and combinations thereof; and (c) a cosmetically- and/or pharmaceutically-acceptable topical carrier.

24. The method of claim 23 wherein:

(a) $R^2$ and $R^3$ are selected from the group consisting of $CH_3$, $CH_2CH_2OH$ and $CH_2CH_2CH_2OH$;

(b) X is $CO_2$ or $SO_3$;

(c) m is 2 or 3; and (d) the sulfhydryl compound is selected from the group consisting of N-acetyl-L-cysteine, glutathione, cosmetically- and/or pharmaceutically-acceptable salts of any of the foregoing compounds, and combinations thereof.

25. The method of claim 24 wherein:

(a) the amount of sulfhydryl compound applied is from about 0.004 mg/cm$^2$ skin to about 0.1 mg/cm$^2$ skin; and (b) the amount of zwitterionic surfactant applied is from about 0.004 mg/cm$^2$ skin to about 0.1 mg/cm$^2$ skin.

* * * * *

UNITED STATES PATENT AND TRADEMARK OFFICE
CERTIFICATE OF CORRECTION

PATENT NO. : 5,681,852
DATED : 10/28/97
INVENTOR(S) : Bissett.

It is certified that error appears in the above-identified patent and that said Letters Patent is hereby corrected as shown below:

In Col. 10, line 28, "mount" should read --amount--.

In Col. 10, line 40, the first occurrence of "parsben" should read --paraben--.

In Col. 10, line 40, the second occurrence of "parsben" should read --paraben--.

Signed and Sealed this

Eighteenth Day of May, 1999

Attest:

Q. TODD DICKINSON

*Attesting Officer*   *Acting Commissioner of Patents and Trademarks*